(12) United States Patent
Bratz et al.

(10) Patent No.: US 6,479,437 B1
(45) Date of Patent: Nov. 12, 2002

(54) HERBICIDAL MIXTURE CONTAINING A 3-HETEROCYCLYL-SUBSTITUTED BENZOYL DERIVATIVE

(75) Inventors: Matthias Bratz, Limburgerhof (DE); Rainer Berghaus, Speyer (DE); Martina Otten, Ludwigshafen (DE); Bernd Sievernich, Böhl-Iggelheim (DE); Elmar Kibler, Hassloch (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/701,875

(22) PCT Filed: May 27, 1999

(86) PCT No.: PCT/EP99/03676

§ 371 (c)(1), (2), (4) Date: Dec. 5, 2000

(87) PCT Pub. No.: WO99/63823

PCT Pub. Date: Dec. 16, 1999

(30) Foreign Application Priority Data

Jun. 9, 1998 (DE) .......................... 198 25 588

(51) Int. Cl.[7] .................. A01N 43/56; A01N 43/78; A01N 43/80

(52) U.S. Cl. .................. 504/266; 504/269; 504/271

(58) Field of Search .............. 504/266, 269, 504/271

(56) References Cited

U.S. PATENT DOCUMENTS 5,658,855 A   8/1997   Nalewaja et al. .......... 504/214

FOREIGN PATENT DOCUMENTS

| EP | 584 227 | 3/1994 |
|---|---|---|
| SU | 701626 | 12/1979 |
| WO | WO 92/19107 | 11/1992 |
| WO | WO 96/26206 | 8/1996 |
| WO | WO 97/41116 | 11/1997 |
| WO | WO 97/41117 | 11/1997 |
| WO | WO 97/41118 | 11/1997 |

OTHER PUBLICATIONS

Klingman et al. Weed Science: Principles and Practices. 2nd ed. NY:John Wiley & Sons. p. 106–107,294. 1982.*

* cited by examiner

Primary Examiner—S. Mark Clardy
(74) Attorney, Agent, or Firm—Keil & Weinkauf

(57) ABSTRACT

A herbicidal mixture comprising
a) a herbicidally active amount of a 3-heterocyclyl-substituted benzoyl derivative of the formula I

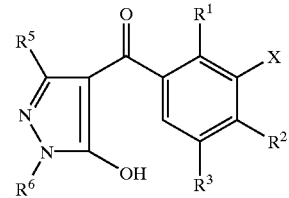

in which the variables have the following meanings:
$R^1$, $R^2$ are hydrogen, halogen, $C_1$–$C_6$-alkyl, $C_1$–$C_6$-alkylthio, $C_1$–$C_6$-alkylsulfinyl, $C_1$–$C_6$-alkylsulfonyl, $C_1$–$C_6$-haloalkyl, $C_1$–$C_6$-alkoxy, $C_1$–$C_6$-haloalkoxy;
$R^3$ is hydrogen, halogen, $C_1$–$C_6$-alkyl;
X is a heterocycle from amongst the group consisting of isoxazolyl, 4,5-dihydroisoxazolyl and thiazolyl, it being possible for the heterocycle to be optionally monosubstituted or polysubstituted by halogen, $C_1$–$C_6$-alkyl, $C_1$–$C_4$-alkoxy, $C_1$–$C_4$-haloalkyl, $C_1$–$C_4$-haloalkoxy, $C_1$–$C_4$-alkylthio;
$R^5$ is hydrogen or $C_1$–$C_6$-alkyl,
$R^6$ is $C_1$–$C_6$-alkyl,
or their environmentally compatible salts;
b) a nitrogenous fertilizer in a synergistically effective amount and
c) an adjuvant in a synergistically effective amount.

11 Claims, No Drawings

HERBICIDAL MIXTURE CONTAINING A 3-HETEROCYCLYL-SUBSTITUTED BENZOYL DERIVATIVE

This application is a 371 of PCT/EP99/03676 filed May 27, 1999.

The present invention relates to a synergistically acting herbicidal mixture of a 3-heterocyclyl-substituted benzoyl derivative, a nitrogenous fertilizer and an adjuvant.

3-Heterocyclyl-substituted benzoyl derivatives are known and are described, for example, in WO 96/26206, WO 97/41116, WO 97/41117 and WO 97/41118.

Herbicidal compositions of substituted cyclohexanediones and nitrogen fertilizers are disclosed in EP-B-0584 227.

It is an object of the present invention to provide a herbicidal mixture which comprises 3-heterocyclyl-substituted benzoyl derivatives and whose herbicidal action exceeds the action of the pure active ingredient.

We have found that this object is achieved by a herbicidal mixture which comprises
a) a herbicidally active amount of a 3-heterocyclyl-substituted benzoyl derivative of the formula I

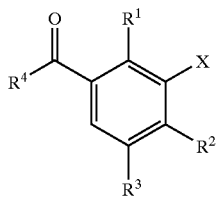

in which the variables have the following meanings:
$R^1, R^2$ are hydrogen, halogen, $C_1$–$C_6$-alkyl, $C_1$–$C_6$-alkylthio, $C_1$–$C_6$-alkylsulfinyl, $C_1$–$C_6$-alkylsulfonyl, $C_1$–$C_6$-haloalkyl, $C_1$–$C_6$-alkoxy, $C_1$–$C_6$-haloalkoxy;
$R^3$ is hydrogen, halogen, $C_1$–$C_6$-alkyl;
X is a heterocycle from amongst the group consisting of isoxazolyl, 4,5-dihydroisoxazolyl and thiazolyl, it being possible for the heterocycle to be optionally monosubstituted or polysubstituted by halogen, $C_1$–$C_6$-alkyl, $C_1$–$C_4$-alkoxy, $C_1$–$C_4$-haloalkyl, $C_1$–$C_4$-haloalkoxy, $C_1$–$C_4$-alkylthio;
$R^4$ is a pyrazole of the formula II

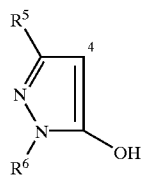

which is linked in the 4-position and where
$R^5$ is hydrogen or $C_1$–$C_6$-alkyl,
$R^6$ is $C_1$–$C_6$-alkyl or their environmentally compatible salts;
b) a nitrogenous fertilizer in a synergistically effective amount and
c) an adjuvant in a synergistically effective amount.

The herbicidal mixture according to the invention exhibits a synergistic effect and is selective for those crop plants which also tolerate the individual compounds themselves.

3-Heterocyclyl-substituted benzoyl derivatives of the formula Ib which are especially preferred with a view to the synergistic herbicidal action are those in which

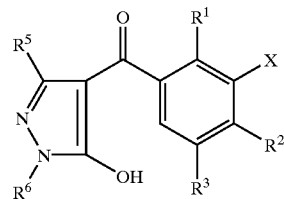

$R^1, R^2$ are chlorine, methyl, ethyl, $SCH_3$, $SOCH_3$, $SO_2CH_3$;
$R^3$ is hydrogen and methyl;
$R^5$ is hydrogen, methyl, trifluoromethyl;
$R^6$ is methyl, ethyl, isopropyl;
X is a heterocycle from amongst the group: isoxazolyl, 4,5-dihydroisoxazolyl and thiazolyl, it being possible for the heterocycle to be optionally monosubstituted or polysubstituted by halogen, $C_1$–$C_6$-alkyl, $C_1$–$C_4$-alkoxy, $C_1$–$C_4$-haloalkyl, $C_1$–$C_4$-haloalkoxy, $C_1$–$C_4$-alkylthio,
or their environmentally compatible salts.

Preferred compounds of the formula Ib are compiled in the table which follows:

| No | $R_1$ | $R_2$ | $R_3$ | $R_5$ | $R_6$ | X |
|---|---|---|---|---|---|---|
| 1 | Cl | $SO_2CH_3$ | H | $CH_3$ | $CH_3$ | 2-thiazolyl |
| 2 | Cl | $SO_2CH_3$ | H | H | $CH_3$ | 2-thiazolyl |
| 3 | Cl | $SO_2CH_3$ | H | $CH_3$ | $CH_3$ | 4,5-dihydroisoxazol-3-yl |
| 4 | Cl | Cl | H | $CH_3$ | $CH_3$ | 4,5-dihydroisoxazol-3-yl |
| 5 | Cl | $SO_2CH_3$ | H | H | $CH_3$ | 4,5-dihydroisoxazol-3-yl |
| 6 | Cl | $SO_2CH_3$ | H | H | $CH_3$ | 4,5-dihydro-5-methylisoxazol-3-yl |
| 7 | Cl | $SO_2CH_3$ | H | H | $CH_3$ | 4,5-dihydro-5,5-dimethylisoxazol-3-yl |
| 8 | Cl | $SO_2CH_3$ | H | H | $CH_3$ | 4,5-dihydro-5-ethylisoxazol-3-yl |
| 9 | Cl | $SO_2CH_3$ | H | H | $CH_3$ | 4,5-dihydro-5,5-diethylisoxazol-3-yl |
| 10 | Cl | $SO_2CH_3$ | H | H | $CH_3$ | 4,5-dihydro-5-chloromethylisoxazol-3-yl |
| 11 | Cl | $SCH_3$ | H | H | $CH_3$ | 4,5-dihydroisoxazol-3-yl |
| 12 | Cl | $SO_2CH_3$ | H | H | $CH_3$ | 4,5-dihydro-5-ethoxyisoxazol-3-yl |
| 13 | Cl | $SO_2CH_3$ | H | H | $CH_3$ | 4,5-dihydro-5-methoxyisoxazol-3-yl |
| 14 | $CH_3$ | $SO_2CH_3$ | H | H | $CH_3$ | 4,5-dihydroisoxazol-3-yl |
| 15 | Cl | $SO_2CH_3$ | H | H | $CH_3$ | 4,5-dihydro-4,5-dimethylisoxazol-3-yl |
| 16 | Cl | $SO_2CH_3$ | H | H | $CH_3$ | 4,5-dihydro-5-thioethylisoxazol-3-yl |
| 17 | Cl | $SO_2CH_3$ | H | H | $CH_3$ | 4,5-dihydro-5-trifluoromethylisoxazol-3-yl |
| 18 | $SCH_3$ | $SCH_3$ | H | H | $CH_3$ | 4,5-dihydroisoxazol-3-yl |
| 19 | Cl | $SO_2CH_3$ | H | H | $C_2H_5$ | 2-thiazolyl |
| 20 | Cl | $SO_2CH_3$ | H | H | $C_2H_5$ | 4,5-dihydroisoxazol-3-yl |
| 21 | Cl | $SO_2CH_3$ | H | H | $C_2H_5$ | 4,5-dihydro-5-methylisoxazol-3-yl |
| 22 | Cl | $SO_2CH_3$ | H | H | $C_2H_5$ | 4,5-dihydro-5,5-dimethylisoxazol-3-yl |
| 23 | Cl | $SO_2CH_3$ | H | H | $C_2H_5$ | 4,5-dihydro-5-ethylisoxazol-3-yl |
| 24 | Cl | $SO_2CH_3$ | H | H | $C_2H_5$ | 4,5-dihydro-5,5-diethylisoxazol-3-yl |
| 25 | Cl | $SCH_3$ | H | H | $C_2H_5$ | 4,5-dihydroisoxazol-3-yl |
| 26 | Cl | $SO_2CH_3$ | H | H | $C_2H_5$ | 4,5-dihydro-5-chloromethylisoxazol-3-yl |
| 27 | Cl | $SO_2CH_3$ | H | H | $C_2H_5$ | 4,5-dihydro-5-ethoxyisoxazol-3-yl |

-continued

| No | R₁ | R₂ | R₃ | R₅ | R₆ | X |
|---|---|---|---|---|---|---|
| 28 | Cl | SO₂CH₃ | H | H | C₂H₅ | 4,5-dihydro-4,5-dimethyl-isoxazol-3-yl |
| 29 | CH₃ | SO₂CH₃ | H | H | C₂H₅ | 4,5-dihydroisoxazol-3-yl |
| 30 | Cl | SO₂CH₃ | H | H | C₂H₅ | 4,5-dihydro-5-thioethyl-isoxazol-3-yl |
| 31 | Cl | SO₂CH₃ | H | H | C₂H₅ | 4,5-dihydro-5-trifluoro-methylisoxazol-3-yl |
| 32 | SCH₃ | SCH₃ | H | H | C₂H₅ | 4,5-dihydroisoxazol-3-yl |
| 33 | Cl | SO₂CH₃ | H | H | i-C₄H₉ | 4,5-dihydroisoxazol-3-yl |
| 34 | Cl | SO₂CH₃ | H | H | CH₃ | 3-methylisoxazol-5-yl |
| 35 | Cl | SO₂CH₃ | H | H | C₂H₅ | 3-methylisoxazol-5-yl |
| 36 | CH₃ | SO₂CH₃ | H | H | C₂H₅ | 3-methylisoxazol-5-yl |
| 37 | CH₃ | SO₂CH₃ | H | CH₃ | CH₃ | 4,5-dihydroisoxazol-3-yl |
| 38 | CH₃ | Cl | H | CH₃ | CH₃ | 4,5-dihydroisoxazol-3-yl |
| 39 | CH₃ | SO₂CH₃ | H | H | CH₃ | 4,5-dihydro-5-methyl-isoxazol-3-yl |
| 40 | CH₃ | SO₂CH₃ | H | H | CH₃ | 4,5-dihydro-5,5-dimethyl-isoxazol-3-yl |
| 41 | CH₃ | SO₂CH₃ | H | H | CH₃ | 4,5-dihydro-5-ethyl-isoxazol-3-yl |
| 42 | CH₃ | SO₂CH₃ | H | H | CH₃ | 4,5-dihydro-5,5-ethyl-isoxazol-3-yl |
| 43 | CH₃ | SO₂CH₃ | H | H | CH₃ | 4,5-dihydroisoxazol-3-yl |
| 44 | CH₃ | SO₂CH₃ | H | H | CH₃ | 4,5-dihydro-4,5-dimethyl-isoxazol-3-yl |
| 45 | CH₃ | Cl | H | H | C₂H₅ | 4,5-dihydroisoxazol-3-yl |
| 46 | CH₃ | SO₂CH₃ | H | H | C₂H₅ | 4,5-dihydro-5-methyl-isoxazol-3-yl |
| 47 | CH₃ | SO₂CH₃ | H | H | C₂H₅ | 4,5-dihydro-5,5-dimethyl-isoxazol-3-yl |
| 48 | CH₃ | SO₂CH₃ | H | H | C₂H₅ | 4,5-dihydro-5-ethyl-isoxazol-3-yl |
| 49 | CH₃ | SO₂CH₃ | H | H | C₂H₅ | 4,5-dihydro-4,5-dimethyl-isoxazol-3-yl |
| 50 | CH₃ | SO₂CH₃ | H | H | i-C₄H₉ | 4,5-dihydroisoxazol-3-yl |

Very especially preferred are the compounds

4-[2-chloro-3-(4,5-dihydroisoxazol-3-yl)-4-methylsulfonylbenzoyl]-1-methyl-5-hydroxy-1H-pyrazole, 4-[2-methyl-3-(4,5-dihydroisoxazol-3-yl)-4-methylsulfonylbenzoyl ]-1-methyl-5-hydroxy-1H-pyrazole, 4-[2-chloro-3-(3-methylisoxazol-5-yl)-4-methylsulfonylbenzoyl]-1-methyl-5-hydroxy-1H-pyrazole, or their environmentally compatible salts.

Suitable environmentally compatible salts are salts of, for example, alkali metals, alkaline earth metals, ammonia or amines.

Suitable nitrogenous fertilizers b) are ammonia and ammonium salts, urea, thiourea and mixtures of these.

Examples of suitable fertilizers are aqueous ammonia solution, ammonium nitrate, ammonium sulfate, ammonium hydrogen sulfate, ammonium chloride, ammonium acetate, ammonium formate, ammonium oxalate, ammonium carbonate, ammonium hydrogen carbonate, ammonium nitrate, ammonium thiosulfate, ammonium phosphate, ammonium hydrogen diphosphate, ammonium dihydrogen monophosphate, ammonium sodium hydrogen phosphate, ammonium thiocyanate, urea and thiourea, and mixtures of these, and also ammonium nitrate/urea solutions (UAN or AHL solutions).

Preferred nitrogenous fertilizers are urea, ammonium nitrate, ammonium nitrate/urea solutions, ammonium sulfate, ammonium phosphate, ammonium hydrogen diphosphate, ammonium dihydrogen monophosphate and ammonium sodium hydrogen phosphate.

Very especially preferred are urea, ammonium nitrate and ammonium nitrate/urea solutions. The ammonium nitrate/urea solutions preferably have a total nitrogen content of 28–33% (w/w) and are commercially available from BASF, for example under the brand name Ensol® 28.

Suitable adjuvants c) are vegetable oils which can be partially hydrogenated and hydrogenated, modified vegetable oils, mineral oils, alcohol alkoxylates, alcohol ethoxylates, alkylated EO/PO block copolymers, alkylphenol ethoxylates, polyols, EO/PO block copolymers, organosilicon compounds, alkylglycosides, alkyl polyglycosides, alkyl sulfates, sulfated alcohol alkoxylates, alkylarylsulfonates, alkylsulfonates, dialkylsulfosuccinates, phosphated alcohol alkoxylates, fatty amine alkoxylates, esters, carboxylates, ester ethoxylates, dialkyl adipates, dicarboxylic acid derivatives, such as alkenylsuccinic anhydride condensates with polyalkylene oxides or polyhydroxyamines; dialkyl phthalates, ethoxylated sorbitan esters of natural fatty acids and ethoxylated glycerides of natural fatty acids.

Preferred adjuvants are alcohol alkoxylates, such as alkyl ethers of EO/PO copolymers, for example Plurafac® (BASF AG), Synperionic® LF (ICI), alcohol ethoxylates, the alcohol being a $C_8$–$C_{18}$-alcohol of synthetic or natural origin which may be either linear or branched. The ethoxylate moiety contains on average 3–20 moles of ethylene oxide, depending on the alcohol used. Products used are, for example, Lutensol® ON, TO, AO and A by BASF, alkylarylsulfonates, such as nonylphenyl ethoxylates with 5–15 moles of EO, polyols such as polyethylene glycol or polypropylene glycol, EO/PO block copolymers such as, for example, Pluronic® PE (BASF AG) or Synperionic® PE (ICI), organosilicon compounds, alkyl polyglycosides, such as, for example, Agrimul® (Henkel KGA), AG 6202 (Akzo-Nobel), Atplus® 450 (ICI) or Lutensol® GD 70 (BASF AG), fatty amine alkoxylates, such as, for example, Ethomeen® and Armobleem® by Akzo Nobel, esters of natural and synthetic fatty acids, such as, for example, methyl oleates or methyl cocoates, dialkyl adipates, ethoxylated sorbitan esters of natural fatty acids, such as, for example, Tween® by ICI Surfactants (Tween® 20, Tween® 85, Tween® 80), ethoxylated glycerides of natural fatty acids, such as, for example, Glycerox® by Croda.

Other examples are found in:

McCutcheon's; Emulsifiers and Detergents, Volume 1: Emulsifiers and Detergents 1994 North American Edition;

McCutcheon's Division, Glen Rock N.J., USA,

McCutcheon's; Emulsifiers and Detergents, Volume 2: Emulsifiers and Detergents 1994 International Edition;

McCutcheon Division, Glen Rock N.J., USA,

Surfactants in Europe;

A Directory of surface active agents available in Europe 2nd Ed. 1989;

Terg Data, Darlington, England,

Ash, Michael;

Handbook of cosmetic and personal care additives 1994;

Gower Publishing Ltd, Aldershot, England

Ash, Michael;

Handbook of industrial Surfactants 1993;

Gower Publishing Ltd. Aldershot, England.

The herbicidal mixture according to the invention comprises the following amounts of the components a) to c):

0.5 to 90% by weight of the 3-heterocyclyl-substituted benzoyl derivative a);

5 to 94.5% by weight of the nitrogenous fertilizer b);

5 to 50% by weight of the adjuvant c).

Preferred weight ratios are:

0.5 to 50% by weight of the 3-heterocyclyl-substituted benzoyl derivative a);

5 to 90% by weight of the nitrogenous fertilizer b);

5 to 50% by weight of the adjuvant c).

The components together add up to 100% by weight.

The individual components a) to c) of the herbicidal mixture according to the invention can be formulated and packaged jointly or individually. Furthermore, it is possible to formulate and pack the components a) together with b), or a) together with c).

The practitioner uses the herbicidal mixture or its individual components for use in the spray tank.

For this purpose, the herbicidal mixture is diluted with water, adding, if appropriate, other auxiliaries and additives. However, the practitioner may also mix the individual components a) to c) of the herbicidal mixture according to the invention himself in the spray tank and, if appropriate, add further auxiliaries and additives (tank mix method).

For the tank mix method, the components a) to c) are mixed in the spray tank and made up to the desired use concentration with water.

The following adjuvants have proved advantageous for the tank mix method:

mineral oils, liquid paraffins, vegetable oils, hydrogenated or methylated vegetable oils, such as, for example, soya oil, rapeseed oil, sunflower oil, esters and salts of natural carboxylic acids, such as, for example, methyl oleate, methylated seed oils, nonionic surfactants, such as ethoxylated alcohols, ethoxylated phenols, fatty amine ethoxylates, and mixtures of these.

Further auxiliaries and additives may be added for better processing. The following components have proved themselves as auxiliaries and additives:

solvents, antifoams, buffers, thickeners, spreading agents, compatibility-enhancing agents.

Examples and brands of adjuvants, auxiliaries and additives are described in Farm Chemicals Handbook 1997; Meister Publishing 1997 p. C10 "adjuvant" or 1998 Weed Control Manual p. 86.

The mixture according to the invention is suitable as herbicide. The herbicidal mixture effects very good control of vegetation on non-crop areas, especially at high rates of application. In crops such as wheat, rice, maize, soybeans and cotton it acts against broad-leaved weeds and grass weeds without damaging the crop plants substantially. This effect is observed especially at low rates of application.

Depending on the application method in question the herbicidal mixture can additionally be employed in a further number of crop plants for eliminating undesirable plants. Examples of suitable crops are the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum* (*N.rustica*), *Olea europaea, Oryza sativa, Phaseolus lunatus, Phaseolus vulgaris, Picea abies,* Pinus spec., *Pisum sativum, Prunus avium, Prunus persica, Pyrus communis, Ribes sylvestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera* and *Zea mays.*

Moreover, the herbicidal mixture can also be used in crops which tolerate the action of herbicides due to breeding including genetic engineering methods.

The herbicidal mixture can be applied pre- or post-emergence. If the herbicidal mixture is less well tolerated by certain crop plants, application techniques may be used in which the herbidical mixture is sprayed, with the aid of the spray apparatus, in such a way that it comes into little contact, if any, with the leaves of the sensitive crop plants while reaching the leaves of undesirable plants which grow underneath, or the bare soil (post-directed, lay-by).

The herbicidal mixture can be employed, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, spreading or pouring. The use forms depend on the intended purposes; in any case, they should guarantee the finest possible distribution of the herbicidal mixture according to the invention.

Suitable inert auxiliaries are essentially: mineral oil fractions of medium to high boiling point such as kerosene and diesel oil, furthermore coal tar oils and oils of vegetable or animal origin, aliphatic, cyclic and aromatic hydrocarbons, e.g. paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone, or strongly polar solvents, e.g. amines such as N-methylpyrrolidone and water.

Aqueous use forms can be prepared from emulsion concentrates, suspensions, pastes, wettable powders or water-dispersible granules by adding water. To prepare emulsions, pastes or oil dispersions, the herbicidal mixture, as such or dissolved in an oil or solvent, can be homogenized in water by means of wetting agent, tackifier, dispersant or emulsifier. However, it is also possible to prepare concentrates composed of active substance, wetting agent, tackifier, dispersant or emulsifier and, if appropriate, solvent or oil, and these concentrates are suitable for dilution with water.

Suitable surfactants are the alkali metal, alkaline earth metal and ammonium salts of aromatic sulfonic acids, e.g. lignosulfonic acid, phenolsulfonic acid, naphthalenesulfonic acid and dibutylnaphthalenesulfonic acid, and of fatty acids, of alkyl- and alkylarylsulfonates, of alkyl sulfates, lauryl ether sulfates and fatty alcohol sulfates, and salts of sulfated hexa-, hepta- and octadecanols, and of fatty alcohol glycol ether, condensates of sulfonated naphthalene and its derivatives with formaldehyde, condensates of naphthalene, or of the naphthalenesulfonic acids, with phenol and formaldehyde, polyoxyethylene octylphenyl ether, ethoxylated isooctyl-, octyl- or nonylphenol, alkylphenyl and tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or concomitantly grinding the herbicidal mixture with a solid carrier.

Granules, e.g. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas and products of vegetable origin such as cereal meal, tree bark meal, wood meal and nutshell meal, cellulose powder or other solid carriers.

The concentrations of the herbicidal mixture in the ready-to-use products can be varied within wide ranges. In general, the formulations comprise approximately from 0.001 to 98% by weight, preferably 0.01 to 95% by weight, of the herbicidal mixture. The components of the mixture are employed in a purity of from 90% to 100%, preferably 95% to 100% (according to NMR spectrum).

The herbicidal mixture according to the invention can be formulated, for example, as follows:

A) Concentrates for Preparing the Mixture According to the Invention

1) Suspension Concentrate 108 g of 4-[2-chloro-3-(4,5-dihydroisoxazol-3-yl)-4-methyl-sulfonylbenzoyl]-1-methyl-5-hydroxy-1H-pyrazole (technical grade 92%), 20 g/l of Wettol® D1 by BASF, 30 g of Pluronic® PE 10500 by BASF AG, 3 g of Kelzan®, 1.4 g of Kathon® MK, 70 g of 1,2-propylene glycol and 5 g of silicone emulsion by Wacker were made up to 1 liter with water and the mixture was subsequently ground in a ball mill to a particle size of 60% <2 microns.

2) Suspension Concentrate 503 g of 4-[2-chloro-3-(4,5-dihydroisoxazol-3-yl)-4-methyl-sulfonylbenzoyl]-1-methyl-5-hydroxy-1H-pyrazole (technical grade 99%), 20 g/l of Wettol® DI by BASF, 30 g of Pluronic® PE 10500 by BASF AG, 3 g of Kelzan®, 1.4 g of Kathon® MK, 70 g of 1,2-propylene glycol and 5 g of silicone emulsion by Wacker were made up to 1 liter with water and the mixture was subsequently ground in a ball mill to a particle size of 60%<2 microns.

3) Water-soluble Concentrate of Component a)

100 g of the active ingredient 4-[2-chloro-3-(4,5-dihydroisoxazol-3-yl)-4-methylsulfonylbenzoyl]-1-methyl-5-hydroxy-1H-pyrazole (99% technical grade) are dispersed in approx. 800 ml of water. The active ingredient is neutralized with dilute potassium hydroxide solution (KOH), and the formulation brought to pH 8.5. The product is then made up to 1 liter.

B) Herbicidal Mixtures According to the Invention

4) Suspension Concentrate 100 ml of the concentrate prepared as described under 2) were mixed with 220 ml of water and 360 ml of ammonium nitrate/urea solution (ENSOL® 28, BASF AG). Using a high-speed stirrer, a solution of 14 g of a calcium dodecylbenzenesulfonate (Wettol® EM 1, BASF AG), 14 g of a castor oil ethoxylate with 40 moles of EO (Wettol® EM 31, BASF AG) and 250 ml of a dioctyl adipate (Plastomoll® DOA, BASF AG) were incorporated into this mixture to give an emulsion. This gave a stable suspension of the 4-[2-chloro-3-(4,5-dihydroisoxazol-3-yl)-4-methylsulfonyl-benzoyl]-1-methyl-5-hydroxy-1H-pyrazole with an active ingredient content of 50 g/l.

5) Suspension Concentrate 100 ml of the concentrate prepared as described under 2) were mixed with 220 ml of water and 360 ml of ammonium nitrate/urea solution (ENSOL® 28, BASF AG). Using a high-speed stirrer, 250 ml of methyl oleate were incorporated into this mixture to give an emulsion. This gave a stable suspension of the 4-[2-chloro-3-(4,5-dihydroisoxazol-3-yl)-4-methylsulfonyl-benzoyl]-1-methyl-5-hydroxy-1H-pyrazole with an active ingredient content of 50 g/l.

6) Water-dispersible Granules 50 g of the active ingredient 4-[2-chloro-3-(4,5-dihydroisoxazol-3-yl)-4-methylsulfonylbenzoyl]-1-methyl-5-hydroxy-1H-pyrazole (99%, technical grade), 50 g of naphthalenesulfonic acid/formaldehyde condensate, 10 g of sodium ligninsulfonate and 600 g of ammonium sulfate are mixed intimately and ground in an air-jet mill. In a mixer, the resulting powder is mixed with 31 g of ethylhexyl glucoside (65% strength aqueous solution). The mixture is extruded in an extruder (DGL-1 by Fitzpatrick, Belgium, aperture diameter 0.8 mm). If appropriate, more liquid is added to achieve extrudability. The granules are dried, and water-dispersible granules with an active ingredient content of 5% are obtained.

7) Water-soluble Concentrate 50 g of the active ingredient 4-[2-chloro-3-(4,5-dihydroisoxazol-3-yl)-4-methylsulfonylbenzoyl]-1-methyl-5-hydroxy-1H-pyrazole (99%, technical grade) are dispersed in 200 ml of water and the mixture is neutralized with dilute potassium hydroxide solution (KOH). This mixture is treated with 360 g of ammonium nitrate/urea solution (ENSOL® 28, BASF AG) and 250 g of Lutensol® ON 80 (BASF AG). The product is brought to pH 8.5 using KOH and made up to 1 liter with water.

8) Water-soluble Concentrate 100 g of the active ingredient 4-[2-chloro-3-(4,5-dihydroisoxazol-3-yl)-4-methylsulfonylbenzoyl]-1-methyl-5-hydroxy-1H-pyrazole (99% technical grade) are dispersed in approx. 300 ml of water. The active ingredient is neutralized with dilute potassium hydroxide solution (KOH) and the formulation is brought to pH 8.5. 500 g of AG 6202 are incorporated into the formulation by stirring. After homogenization, the pH is rechecked and, if necessary, corrected. The product is then made up to 1 liter.

To widen the spectrum of action and to achieve synergistic effects, the herbicidal mixture can be mixed and applied jointly with a large number of representatives of other groups of herbicidally or growth-regulatory active ingredients. Suitable components in mixtures are, for example, 1,2,4-thiadiazoles, 1,3,4-thiadiazoles, amides, aminophosphoric acid and its derivatives, aminotriazoles, anilides, (het)-aryloxyalkanoic acids and their derivatives, benzoic acid and its derivatives, benzothiadiazinones, 2-aroyl-1,3-cyclohexandiones, hetaryl aryl ketones, benzylisoxazolidinones, meta-$CF_3$-phenyl derivates, carbamates, quinolinecarboxylic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- or heteroaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonylureas, triazines, triazinones, triazolinones, triazolecarboxamides and uracils.

Moreover, it may be advantageous to apply the herbicidal mixture, alone or in combination with other herbicides, in the form of a mixture with additional other crop protection agents, for example with pesticides or agents for controlling phytophathogenic fungi or bacteria. Also of interest is the miscibility with mineral salt solutions which are employed for treating nutritional and trace element deficiencies.

The application rate of herbicidal mixture amounts to 0.001 to 1.0, preferably 0.01 to 0.5, kg/ha active substance (a. s.), based on the pure components of the herbicidal mixture, depending on the intended aim, the season, the target plants and the growth stage.

Use example

The herbicidal action of the compositions according to the invention was demonstrated by greenhouse experiments:

The culture containers used were plastic pots containing loamy sand with approximately 3.0% of humus as substrate. The seeds of the test plants were sown separately for each species.

For the pre-emergence treatment, the herbicidal mixture, suspended or emulsified in water, was applied directly after sowing by means of finely distributing nozzles. The containers were irrigated gently to promote germination and growth and subsequently covered with translucent plastic hoods until the plants had rooted. This cover caused uniform germination of the test plants unless this was adversely affected by the herbicidal mixture.

For the post-emergence treatment, the test plants were grown to a plant height of from 3 to 15 cm, depending on the plant habit, and only then treated with the herbicidal mixture which had been suspended or emulsified in water. To this end, the test plants were either sown directly and grown in the same containers, or they were first grown separately as seedlings and transplanted into the test containers a few days prior to treatment.

Depending on the species, the plants were kept at 10–25° C. or 20–35° C. The test period extended over 2 to 4 weeks. During this time, the plants were tended, and their response to the individual treatments was evaluated.

Evaluation was carried out using a scale of from 0 to 100. 100 means no emergence of the plants, or complete destruction of at least the aerial parts, and 0 means no damage or normal course of growth.

The plants used in the greenhouse experiments belonged to the following species:

| Abbreviation | Scientific name | Common name |
|---|---|---|
| ABUTH | Abutilon theophrasti | velvetleaf |
| CHEAL | Chenopodium album | lambsquarters (goosefoot) |
| ECHCG | Echinochloa crus-galli | barnyardgrass |
| POLPE | Polygonum persicaria | lady's thumb |
| SETVI | Setaria viridis | green foxtail |
| ZEAMX | Zea mays | corn |

Example 1

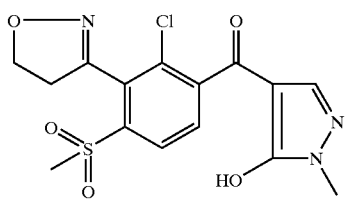

TABLE 1

Selective herbicidal activity post-emergence in the greenhouse

| Active ingredient | Rate of a.s. in kg/ha | Phytotoxicity ZEAMX | Phytotoxicity CHEAL |
|---|---|---|---|
| EX. 1 | 0.0078 | 0 | 20 |
| EX. 1 + Pluronic ® PE 6400 | 0.0078 + 0.25 | 0 | 90 |
| EX. 1 + Pluronic ® PE 6400 + ENSOL ® 28 | 0.0078 + 0.25 + 0.375 | 0 | 95 |

TABLE 2

Selective herbicidal activity post-emergence in the greenhouse

| Active ingredient | Rate of a.s. in kg/ha | Phytotoxicity ZEAMX | Phytotoxicity CHEAL |
|---|---|---|---|
| EX. 1 | 0.0625 | 0 | 50 |
| EX. 1 + Pluronic ® PE 6800 | 0.0625 + 0.25 | 0 | 75 |
| EX. 1 + Pluronic ® PE 6800 + ENSOL ® 28 | 0.0625 + 0.25 + 0.375 | 0 | 80 |

TABLE 3

Selective herbicidal activity post-emergence in the greenhouse

| Active ingredient | Rate of a.s. in kg/ha | Phytotoxicity ECHCG |
|---|---|---|
| EX. 1 | 0.0625 | 50 |
| EX. 1 + Agrimul ® PG 2067 | 0.0625 + 0.25 | 75 |
| EX. 1 + Agrimul ® PG 2067 + ENSOL ® 28 | 0.0625 + 0.25 + 0.375 | 80 |

TABLE 4

Selective herbicidal activity post-emergence in the greenhouse

| Active ingredient | Rate of a.s. in kg/ha | Phytotoxicity ABUTH |
|---|---|---|
| EX. 1 | 0.0156 | 20 |
| EX. 1 + Agrimul ® PG 2067 | 0.0156 + 0.25 | 70 |
| EX. 1 + Agrimul ® PG 2067 + ENSOL ® 28 | 0.0156 + 0.25 + 0.375 | 80 |

TABLE 5

Selective herbicidal activity post-emergence in the greenhouse

| Active ingredient | Rate of a.s. in kg/ha | Phytotoxicity ECHCG | ABUTH |
|---|---|---|---|
| EX. 1 | 0.0312 | 030 | 75 |
| EX. 1 + Agrimul ® PG 600 | 0.0312 + 0.25 | 40 | 80 |
| EX. 1 + Agrimul ® PG 600 + ENSOL ® 28 | 0.0312 + 0.25 + 0.375 | 70 | 85 |

TABLE 6

Selective herbicidal activity post-emergence in the greenhouse

| Active ingredient | Rate of a.s. in kg/ha | Phytotoxicity CHEAL |
|---|---|---|
| EX. 1 | 0.0078 | 20 |
| EX. 1 + Agrimul ® PG 600 | 0.0078 + 0.25 | 70 |
| EX. 1 + Agrimul ® PG 600 + ENSOL ® 28 | 0.0078 + 0.25 + 0.375 | 98 |

TABLE 7

Selective herbicidal activity post-emergence in the greenhouse

| Active ingredient | Rate of a.s. in kg/ha | Phytotoxicity CHEAL |
|---|---|---|
| EX. 1 | 0.0156 | 20 |
| EX. 1 + Lutensol ® GD 70 | 0.0156 + 0.25 | 90 |
| EX. 1 + Lutensol ® PG 600 + ENSOL ® 28 | 0.0156 + 0.25 + 0.375 | 95 |

TABLE 8

Selective herbicidal activity post-emergence in the greenhouse

| Active ingredient | Rate of a.s. in kg/ha | Phytotoxicity ZEAMX | ECHCG |
|---|---|---|---|
| EX. 1 | 0.0625 | 0 | 50 |
| EX. 1 + AG ® 6202 | 0.0625 + 0.25 | 0 | 60 |
| EX. 1 + AG ® 6202 + ENSOL ® 28 | 0.0625 + 0.25 + 0.375 | 0 | 80 |

TABLE 9

Selective herbicidal activity post-emergence in the greenhouse

| Active ingredient | Rate of a.s. in kg/ha | Phytotoxicity ECHCG |
|---|---|---|
| EX. 1 | 0.0625 | 50 |
| EX. 1 + Lutensol ® ON 30 | 0.0625 + 0.25 | 90 |
| EX. 1 + Lutensol ® ON 30 + ENSOL ® 28 | 0.0625 + 0.25 + 0.375 | 100 |

TABLE 10

Selective herbicidal activity post-emergence in the greenhouse

| Active ingredient | Rate of a.s. in kg/ha | Phytotoxicity CHEAL |
|---|---|---|
| EX. 1 | 0.0078 | 20 |
| EX. 1 + Lutensol ® ON 80 | 0.0078 + 0.25 | 80 |
| EX. 1 + Lutensol ® ON 80 + ENSOL ® 28 | 0.0078 + 0.25 + 0.375 | 98 |

TABLE 11

Selective herbicidal activity post-emergence in the greenhouse

| Active ingredient | Rate of a.s. in kg/ha | Phytotoxicity SETVI | CHEAL |
|---|---|---|---|
| EX. 1 | 0.0078 | 30 | 20 |
| EX. 1 + Lutensol ® ON 110 | 0.0078 + 0.25 | 40 | 60 |
| EX. 1 + Lutensol ® ON 110 + ENSOL ® 28 | 0.0078 + 0.25 + 0.375 | 95 | 95 |

TABLE 12

Selective herbicidal activity post-emergence in the greenhouse

| Active ingredient | Rate of a.s. in kg/ha | Phytotoxicity CHEAL |
|---|---|---|
| EX. 1 | 0.0156 | 20 |
| EX. 1 + Lutensol ® TO 8 | 0.0156 + 0.25 | 50 |
| EX. 1 + Lutensol ® TO 8 + ENSOL ® 28 | 0.0156 + 0.25 + 0.375 | 80 |

TABLE 13

Selective herbicidal activity post-emergence in the greenhouse

| Active ingredient | Rate of a.s. in kg/ha | Phytotoxicity CHEAL |
|---|---|---|
| EX. 1 | 0.0156 | 20 |
| EX. 1 + Pluriol ® E 600 | 0.0156 + 0.25 | 60 |
| EX. 1 + Pluriol ® E 600 + ENSOL ® 28 | 0.0156 + 0.25 + 0.375 | 98 |

TABLE 14

Selective herbicidal activity post-emergence in the greenhouse

| Active ingredient | Rate of a.s. in kg/ha | Phytotoxicity CHEAL |
|---|---|---|
| EX. 1 | 0.0156 | 20 |
| EX. 1 + Pluriol ® E 4000 | 0.0156 + 0.25 | 90 |
| EX. 1 + Pluriol ® E 4000 + ENSOL ® 28 | 0.0156 + 0.25 + 0.375 | 98 |

TABLE 15

Selective herbicidal activity post-emergence in the greenhouse

| Active ingredient | Rate of a.s. in kg/ha | Phytotoxicity ECHCG |
|---|---|---|
| EX. 1 | 0.0625 | 50 |
| EX. 1 + Glycerox ® L 8 | 0.0625 + 0.25 | 85 |
| EX. 1 + Glycerox ® L 8 + ENSOL ® 28 | 0.0625 + 0.25 + 0.375 | 90 |

TABLE 16

Selective herbicidal activity post-emergence in the greenhouse

| Active ingredient | Rate of a.s. in kg/ha | Phytotoxicity ABUTH |
|---|---|---|
| EX. 1 | 0.0156 | 20 |
| EX. 1 + Glycerox ® L 8 | 0.0156 + 0.25 | 70 |
| EX. 1 + Glycerox ® L 8 + ENSOL ® 28 | 0.0156 + 0.25 + 0.375 | 80 |

TABLE 17

Selective herbicidal activity post-emergence in the greenhouse

| Active ingredient | Rate of a.s. in kg/ha | Phytotoxicity SETVI | Phytotoxicity POLPE |
|---|---|---|---|
| EX. 1 | 0.0078 | 30 | 20 |
| EX. 1 + Glycerox ® HE | 0.0078 + 0.25 | 20 | 40 |
| EX. 1 + Glycerox ® HE + ENSOL ® 28 | 0.0078 + 0.25 + 0.375 | 95 | 95 |

TABLE 18

Selective herbicidal activity post-emergence in the greenhouse

| Active ingredient | Rate of a.s. in kg/ha | Phytotoxicity POLPE |
|---|---|---|
| EX. 1 | 0.0078 | 70 |
| EX. 1 + Plastomoll ® DOA | 0.0078 + 0.25 | 80 |
| EX. 1 + Plastomoll ® DOA + ENSOL ® 28 | 0.0078 + 0.25 + 0.375 | 95 |

TABLE 19

Selective herbicidal activity post-emergence in the greenhouse

| Active ingredient | Rate of a.s. in kg/ha | Phytotoxicity SETVI | Phytotoxicity POLPE |
|---|---|---|---|
| EX. 1 | 0.0078 | 40 | 70 |
| EX. 1 + Lutensol ® TO 15 | 0.0078 + 0.25 | 60 | 80 |
| EX. 1 + Lutensol ® TO 15 + ENSOL ® 28 | 0.0078 + 0.25 + 0.375 | 95 | 90 |

TABLE 20

Selective herbicidal activity post-emergence in the greenhouse

| Active ingredient | Rate of a.s. in kg/ha | Phytotoxicity ZEAMX | Phytotoxicity SETVI |
|---|---|---|---|
| EX. 1 | 0.0078 | 0 | 40 |
| EX. 1 + Lutensol ® AT 11 | 0.0078 + 0.25 | 0 | 55 |
| EX. 1 + Lutensol ® AT 11 + ENSOL ® 28 | 0.0078 + 0.25 + 0.375 | 0 | 95 |

TABLE 21

Selective herbicidal activity post-emergence in the greenhouse

| Active ingredient | Rate of a.s. in kg/ha | Phytotoxicity SETVI | POLPE |
|---|---|---|---|
| EX. 1 | 0.0078 | 40 | 70 |
| EX. 1 + Lutensol ® AT 25 | 0.0078 + 0.25 | 45 | 90 |
| EX. 1 + Lutensol ® AT 25 + ENSOL ® 28 | 0.0078 + 0.25 + 0.375 | 90 | 95 |

Legend to the adjuvants employed:

| Name | | |
|---|---|---|
| Pluronic ® PE 6400 | BASF AG | EO/PO block copolymer |
| Pluronic ® PE 6800 | BASF AG | EO/PO block copolymer |
| Agrimul ® PG 2067 | Henkel | alkyl glycoside APG |
| Agrimul ® PG 600 | Henkel | alkyl glycoside APG |
| AG ® 6202 | Akzo | alkyl glycoside APG |
| Lutensol ® GD 70 | BASF AG | alkyl glycoside APG |
| Lutensol ® ON 30 | BASF AG | alkyl ethoxylate |
| Lutensol ® ON 80 | BASF AG | alkyl ethoxylate |
| Lutensol ® ON 110 | BASF AG | alkyl ethoxylate |
| Lutensol ® TO 8 | BASF AG | alkyl ethoxylate |
| Lutensol ® TO 15 | BASF AG | alkyl ethoxylate |
| Lutensol ® AT 11 | BASF AG | alkyl ethoxylate |
| Lutensol ® AT 25 | BASF AG | alkyl ethoxylate |
| Pluriol ® E 600 | BASF AG | polyethylene glycol |
| Pluriol ® E 4000 | BASF AG | polyethylene glycol |
| Plastomoll ® DOA | BASF AG | dioctyl adipate |
| Glycerox ® L 8 | Croda | ethoxylated monoglyceride |
| Glycerox ® HE | Croda | ethoxylated monoglyceride |
| ENSOL ® 28 | BASF AG | ammonium nitrate/urea solution (total nitrogen 28%) |

The values in Tables 1 to 21 demonstrate clearly the synergistic effect of the herbicidal mixture according to the invention in comparison with the corresponding two-way mixtures and in comparison with the pure active ingredient while simultaneously being highly selective in the crop plant maize.

We claim:

1. A herbicidal mixture comprising
   a) a herbicidally active amount of a 3-heterocyclyl-substituted benzoyl derivative of the formula I

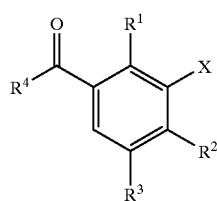

in which the variables have the following meanings:
$R^1, R^2$ are hydrogen, halogen, $C_1$-C6-alkyl, $C_1$-$C_6$-alkylthio, $C_1$-$C_6$-alkylsulfinyl, $C_1$-$C_6$-alkylsulfonyl, $C_1$-$C_6$-haloalkyl, $C_1$-$C_6$-alkoxy, $C_1$-$C_6$-haloalkoxy;
$R^3$ is hydrogen, halogen, $C_1$-$C_6$-alkyl;
X is a heterocycle from amongst the group consisting of isoxazolyl, 4,5-dihydroisoxazolyl and thiazolyl, it being possible for the heterocycle to be optionally monosubstituted or polysubstituted by halogen, $C_1$-$C_6$-alkyl, $C_1$-$C_4$-alkoxy, $C_1$-$C_4$-haloalkyl, $C_1$-$C_4$-haloalkoxy, $C_1$-$C_4$-alkylthio;
$R^4$ is a pyrazole of the formula II

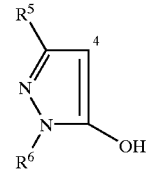

which is linked in the 4-position and where
$R^5$ is hydrogen or $C_1$-$C_6$-alkyl,
$R^6$ is $C_1$-$C_6$-alkyl,
or their environmentally compatible salts;
   b) a nitrogenous fertilizer in a synergistically effective amount and
   c) an adjuvant in a synergistically effective amount.

2. A herbicidal mixture as claimed in claim 1, comprising a 3-heterocyclyl-substituted benzoyl derivative of the formula I as claimed in claim 1 where $R^3$ is hydrogen.

3. A herbicidal mixture as claimed in claim 1, comprising a 3-heterocyclyl-substituted benzoyl derivative of the formula I as claimed in claim 1, where
$R^1, R^2$ are halogen, $C_1$-$C_6$-alkyl, $C_1$-$C_6$-alkylthio, $C_1$-$C_6$-alkylsulfinyl, $C_1$-$C_6$-alkylsulfonyl.

4. A herbicidal mixture as claimed in claim 1, comprising a 3-heterocyclyl-substituted benzoyl derivative of the formula I as claimed in claim 1 where X is isoxazolyl and 4,5-dihydroisoxazolyl, each of which can optionally be substituted by $C_1$-$C_6$-alkyl.

5. A herbicidal mixture as claimed in claim 1, comprising a 3-heterocyclyl-substituited benzoyl derivative of the formula I as claimed in claim 1 where X is isoxazol-5-yl, 3-methylisoxazol-5-yl, 4,5-dihydroisoxazol-3-yl, 4,5-dihydro-5-methylisoxazol-3-yl, 4,5-dihydro-5-ethylisoxazol-3-yl, 4,5-dihydro-4,5-dimethylisoxazol-3-yl.

6. A herbicidal mixture as claimed in claim 1, comprising 4-[2-chloro-3-(4,5-dihydroisoxazol-3-yl)-4-methylsulfonylbenzoyl]-1-methyl-5-hydroxy-1H-pyrazole.

7. A herbicidal mixture as claimed in claim 1, comprising 4-[2-methyl-3-(4,5-dihydroisoxazol-3-yl)-4-methylsulfonylbenzoyl]-1-methyl-5-hydroxy-1H-pyrazole.

8. A herbicidal mixture as claimed in claim 1, comprising a nitrogenous fertilizer b) selected from the series consisting of ammonia, ammonium salts, urea, thiourea and mixtures of these.

9. A herbicidal mixture as claimed in claim 1, comprising
   0.5–90% by weight of the 3-heterocyclyl-substituted benzoyl derivative a);
   5–94.5% by weight of the nitrogenous fertilizer b);
   5–50% by weight of the adjuvant c).

10. A process for the preparation of a herbicidal mixture as claimed in claim 1, which comprises mixing the components a) to c) of the herbicidal mixture with each other.

11. A method of controlling undesirable vegetation, which comprises mixing a herbicidally active amount of the components a) to c) of the herbicidal mixture as claimed in claim 1 with each other and allowing the mixture to act on the plants or their environment.

* * * * *